United States Patent [19]

White

[11] 4,256,107
[45] Mar. 17, 1981

[54] VAGINAL CLEANSING APPARATUS

[76] Inventor: Ruth White, 923 Second St., Santa Monica, Calif. 90403

[21] Appl. No.: 62,007

[22] Filed: Jul. 30, 1979

[51] Int. Cl.³ ............................................. A61M 7/02
[52] U.S. Cl. ..................................... 128/251; 128/261
[58] Field of Search ............... 128/251, 341, 261, 271; 401/9, 280, 281

[56] References Cited

U.S. PATENT DOCUMENTS

| 1,175,129 | 3/1916 | Crittenden | 128/261 |
| 2,127,094 | 8/1938 | Strauss | 128/251 X |
| 2,336,717 | 12/1943 | Crimmins | 401/281 |
| 2,559,757 | 7/1951 | Chandler | 401/9 |
| 2,711,172 | 6/1955 | Booth | 128/341 X |
| 2,745,127 | 5/1956 | Wulf | 401/281 |

FOREIGN PATENT DOCUMENTS 586737 10/1933 Fed. Rep. of Germany ........... 401/281

Primary Examiner—John D. Yasko
Attorney, Agent, or Firm—Philip Hoffman

[57] ABSTRACT

A vaginal cleansing device comprising a sleeve closed at one end with holes in the wall, and a shaft with a longitudinal bore and channels from the bore to the periphery. The ends of the channels are alignable with the holes in the sleeve when the shaft is seated in the sleeve. The channels are slanted so that when aligned as aforesaid cleansing fluid can flow gently from the bore to the vaginal wall.

5 Claims, 6 Drawing Figures

VAGINAL CLEANSING APPARATUS

This invention relates to feminine hygiene generally, and more specifically to vaginal douching devices.

Apparatus for vaginal douching are well known, and typically involve mechanisms for flushing the vagina with a cleansing fluid. These mechanisms force the fluid into the vagina rapidly, thereby flushing the vagina, but they also propel infected discharge of the vagina up into the uterine cavity and beyond, providing the possibility of infection to the user. It would be desirable to have a vaginal douching apparatus devoid of said drawback.

Accordingly, it is an object of this invention to provide a vaginal douching apparatus that is gentle and does not cause irritation or trauma to the user.

It is another object of the present invention to provide a vaginal douching apparatus involving a gravity flow means for gently introducing a cleansing fluid to the vaginal walls.

These and other objects and advantages of the invention are achieved by a vaginal cleansing apparatus comprising: a sleeve closed at one end; retrieving means, such as a handle, associated with an open opposite end of the sleeve; brushing means associated with the periphery of the sleeve, such as a multiplicity of bristles, for brushing the vaginal wall; a shaft seated in the sleeve and having a longitudinal bore extending from an open first end thereof to a closed second end thereof; a multiplicity of channels in the shaft extending from the bore to the shaft periphery and slanting toward the open first end, the channels being alignable with the holes in the sleeve; capping means associated with the shaft for capping the open first end; and alignment means associated with the shaft for aligning the channels with the holes.

DESCRIPTION

The invention is described in greater detail in conjunction with the accompanying drawings in which.

Figure 2:
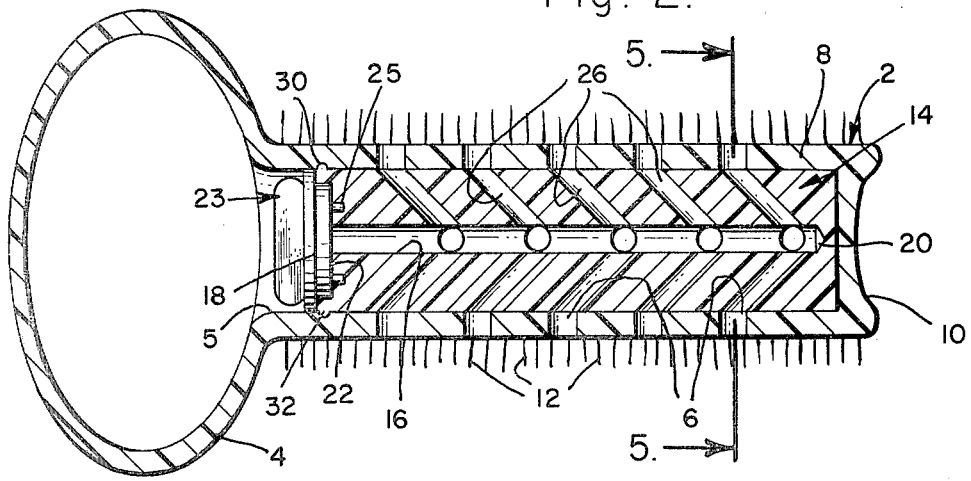
FIG. 2 is a cross-sectional elevational view of the embodiment shown in FIG. 1.
Figure 1:
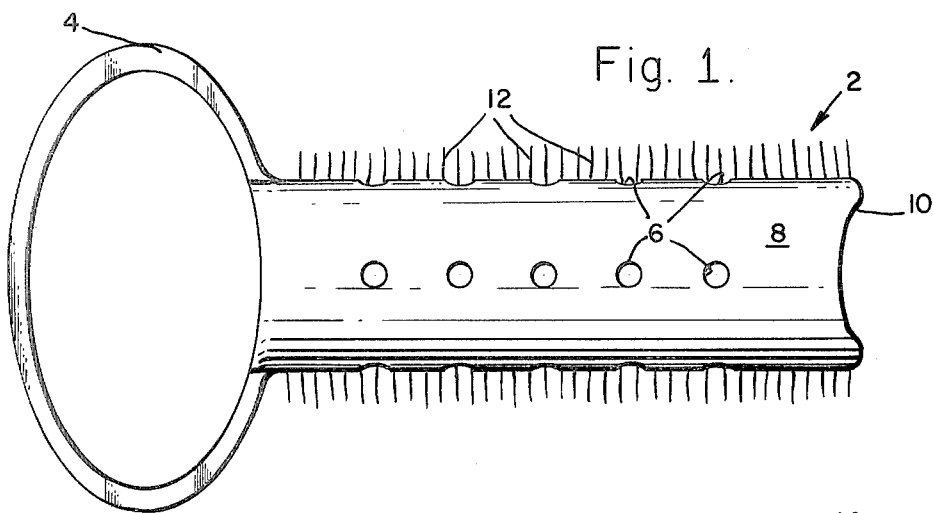
FIG. 1 is an external longitudinal view of an embodiment of the invention.

Referring now to FIGS. 1 and 2 there is shown a sleeve 2 with a flexible handle 4 at an open end 5 and a multiplicity of holes 6 in the side wall 8 thereof. The shape of the sleeve 2 is preferably essentially cylindrical and designed dimensionally to fit the human vagina. The closed end 10 of the sleeve 2 is preferably shaped approximately as shown to conform to the shape of the human cervix. Soft bristles 12 emanate from the side wall 8 and are further discussed below.

Figure 3:
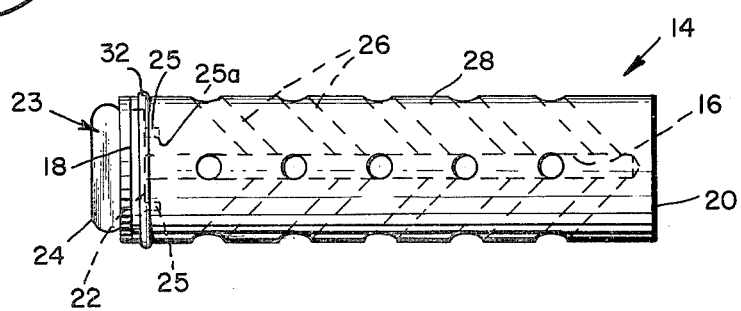
FIG. 3 is an external longitudinal view of the shaft shown in the embodiment of FIG. 2.
Figure 4:
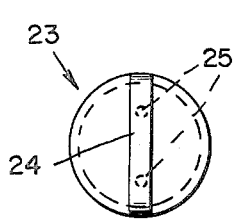
FIG. 4 is an end view of the shaft shown in FIG. 3.

Within the sleeve 2 is an essentially solid shaft 14, shown separately in FIG. 3, with a central longitudinal bore 16 extending from an open end 18 to a closed end 20. The open end 18 comprises an annular seat 22 to accomodate a cap 23 which covers the open end 18. The cap 23 has a finger grip 24, as shown in FIG. 4, which is further discussed below. The cap 23 also has prongs 25 disposed as shown to fit in depressions 25a in the seat 22 so that when the cap 23 is twisted the shaft 14 is easily rotated within the sleeve. The shaft 14 has a multiplicity of channels 26 which extend from said bore 16 to the shaft periphery 28 and slant from said bore 16 toward said open end 18. The sleeve 2 has an annular groove 30 therewithin at the open end 5, and the shaft 14 has an annular bulge 32 therewithout at the open end 18. The bulge 32 is designed to fit the groove 30 so that the shaft 14 is retained in the sleeve 2 and can rotate freely therein.

Figure 6:
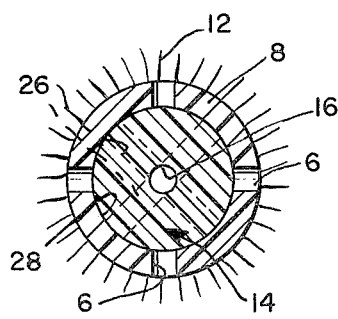
FIG. 6 is a cross-sectional view of the embodiment of FIG. 2 with the shaft rotated from the position shown in FIG. 5.
Figure 5:
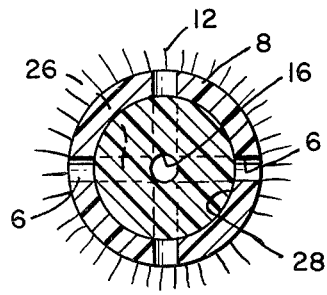
FIG. 5 is a cross-sectional view of the embodiment of FIG. 2 taken along section 5—5.

The apparatus of the invention is used as follows: The shaft 14 is placed in the sleeve 2 (with the bulge 32 secured in the groove 30) so that the channels 26 do not communicate with the holes 6. This position is shown in FIG. 6. The apparatus is held with the handle 4 upward. The cap 23 is removed from the seat 22, and an appropriate vaginal cleansing fluid is poured into the bore 16. When the bore 16 is filled, the cap 23 is replaced, and the device is inserted in the vagina with the handle 4 remaining outside.

The apparatus is now in an essentially inverted position, and because of gravity the tendency of the fluid is to flow from the bore 16 through the channels 26 toward the handle 4. When the channels 26 are next aligned with the holes 6, gravity will cause the fluid to flow through the channels 26 and out the holes 6. The fluid will then come gently in contact with the vaginal wall.

Alignment of the channels 26 and the holes 6 is achieved by appropriately rotating the shaft 14 within the sleeve 2. This rotation is accomplished by holding and twisting the finger grip 24 on the cap 23 until the fluid flows onto the vaginal wall. The cleansing action of the fluid is enhanced by the gentle brushing action of the bristles 12 against the vaginal wall. This occurs when the handle is pulled to retrieve the apparatus from the vagina. The fluid also provides lubrication for the bristles 12 as the apparatus is retrieved.

The apparatus is preferably of polyethelene or other equivalent material which is self lubricating and hypoallergenic. The bristles must be sufficiently soft so as not to irritate the vagina.

There has thus been shown and described a device for vaginal douching. Although specific embodiments of the invention have been described in detail, other variations of the embodiments shown may be made within the spirit, scope and contemplation of the invention.

Accordingly, it is intended that the foregoing disclosure and drawings shall be considered only as illustrations of the principles of this invention and are not to be construed in a limiting sense.

What is claimed is:

1. A vaginal cleansing apparatus for use in a human vagina, comprising:
   a sleeve closed at one end;
   retrieving means associated with an open opposite end of said sleeve for retrieving said apparatus from the vagina;
   a multiplicity of holes in the side wall of said sleeve;
   brushing means associated with the periphery of said sleeve for brushing the vaginal wall;
   an essentially solid shaft seated in said sleeve and having a longitudinal bore extending from an open first end thereof to a closed second end thereof;
   a multiplicity of channels in said shaft extending from said bore to the shaft periphery and slanting toward said open first end, said channels being alignable with said holes in said sleeve;

capping means associated with said shaft for capping said open first end; and alignment means associated with said shaft for aligning said channels with said holes.

2. The apparatus claimed in claim 1 wherein said retrieving means comprises a handle.

3. The apparatus claimed in claim 1 wherein said brushing means comprises a multiplicity of bristles emanating from the periphery of said sleeve.

4. The apparatus claimed in claim 1 wherein said alignment means comprises:
    an annular seat in said open first end of said shaft;
    at least one depression in said seat;
    a cap seated in said seat and having at least one prong engaging said depression; and
    a finger grip associated with said cap such that when held and twisted said shaft rotates in said sleeve.

5. The apparatus claimed in claim 1 wherein said sleeve further comprises an annular groove at said open opposite end, and said shaft further comprises an annular bulge at said open first end, said bulge being seated in said groove when said shaft is seated in said sleeve.

* * * * *